United States Patent [19]
Reif

[11] Patent Number: 5,741,328
[45] Date of Patent: Apr. 21, 1998

[54] PIVOT FOR MECHANICAL HEART VALVE PROTHESIS

[75] Inventor: Thomas H. Reif, Vero Beach, Fla.

[73] Assignee: TRI Technologies Inc., Tortola, Virgin Islands (Br.)

[21] Appl. No.: 712,609

[22] Filed: Sep. 13, 1996

Related U.S. Application Data

[62] Division of Ser. No. 36,687, Mar. 24, 1995, Pat. No. Des. 383,208.

[51] Int. Cl.[6] ................................................ A61F 2/24
[52] U.S. Cl. ....................................................... 623/2
[58] Field of Search ........................................ 623/2, 3

[56] References Cited

U.S. PATENT DOCUMENTS

| | | | |
|---|---|---|---|
| 4,254,508 | 3/1981 | Bokros | 623/2 |
| 4,995,881 | 2/1991 | Knoch et al. | 623/2 |
| 5,147,390 | 9/1992 | Campbell | 623/2 |
| 5,192,313 | 3/1993 | Budd et al. | 623/2 |
| 5,314,467 | 5/1994 | Shu | 623/2 |

*Primary Examiner*—David Isabella
*Attorney, Agent, or Firm*—Albert H. Reuther

[57] ABSTRACT

A pivot mechanism for a mechanical heart prosthesis includes internal recesses on an inside surface of an orifice ring having portions thereof near the recesses tapered to reduce flow resistance and minimize turbulence to improve hemodynamic efficiency of the heart valve prosthesis, to reduce its hemolytic potential, and possibly reduce its thrombogenicity by having no regions of stasis within the recess. The pivot mechanism for the mechanical heart valve prosthesis enables contact between the entire length of tabs of the heart valve leaflets and the sides of the recesses when the leaflets are in both the fully open and fully closed positions. This increases the contact area between the tabs and the recesses, reducing the magnitude of the contact stresses and, therefore, improving the durability of the device. The pivot mechanism minimizes translation of the leaflets to improve hemodynamic efficiency of the device and to reduce the impact forces within the pivot mechanism for improved durability and quieter closure.

11 Claims, 2 Drawing Sheets

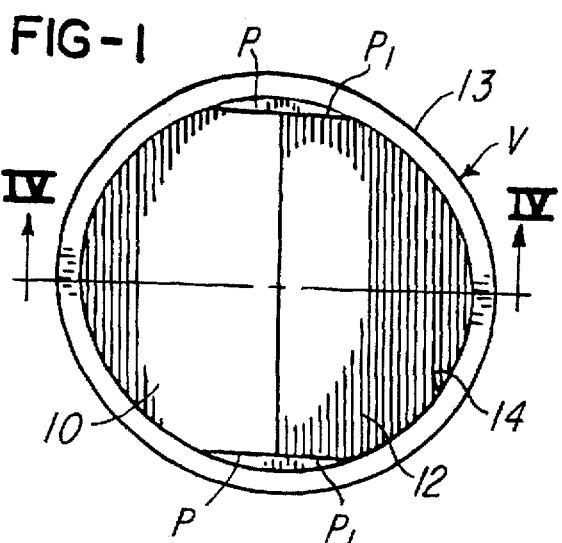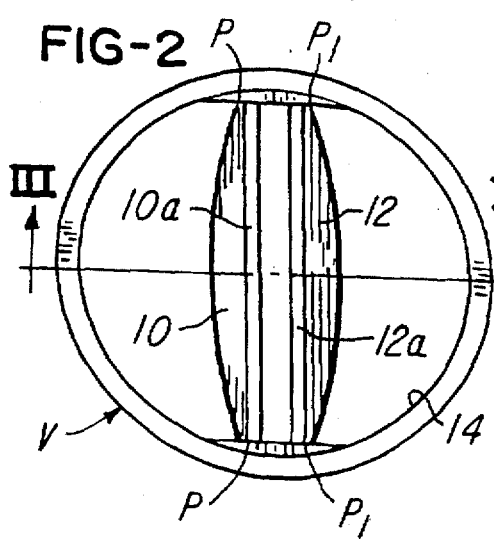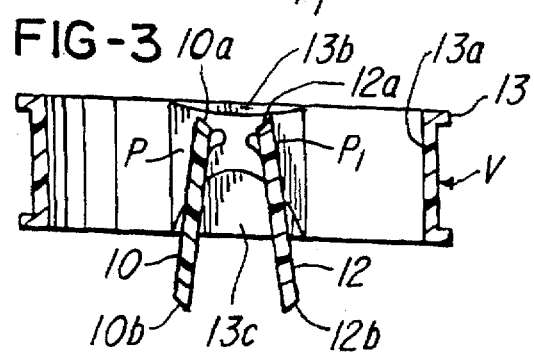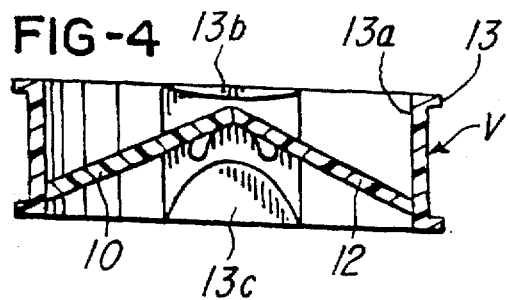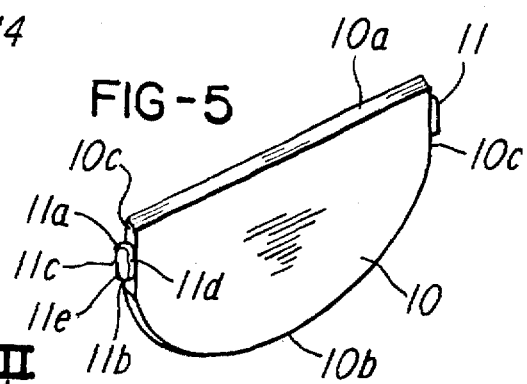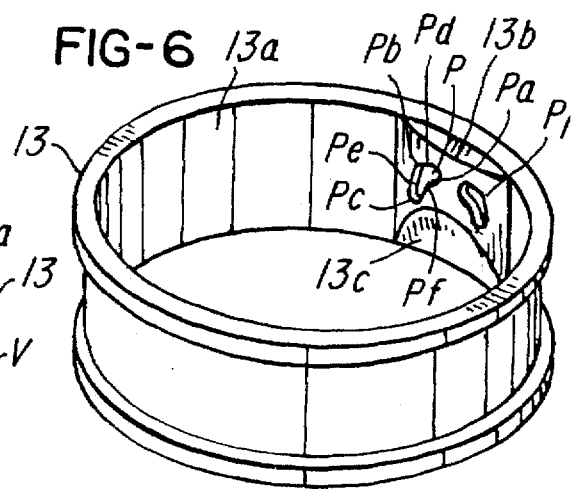

PIVOT FOR MECHANICAL HEART VALVE PROTHESIS

This is a divisional application based upon Design application Ser. No. 036,687-Reif filed Mar. 24, 1995, now U.S. Pat. No. Des. 383,208 for a Heart Valve including an annular body portion of plastic material along an inner periphery having a pair of diametrically oppositely located pivot portions complementary to a pair of bi-leaflet valve flaps.

BACKGROUND OF THE INVENTION

1. Field of the Invention

The present invention relates to a heart valve prostheses, and more particularly, to a pivot mechanism for mechanical heart valve prostheses.

2. Description of the Prior Art

There are two types of heart valve prostheses, biological and mechanical The medical indications for heart valve replacement are the same for both types. Examples include rheumatic heart disease, congenital anomalies, and myocardial infarction.

Unidirectional flow is the primary function of heart, valve prostheses. This is usually accomplished by fashioning rigid or flexible leaflets, free to articulate within certain limitations, within an annular shaped frame, frequently referred to as an orifice ring. The restrained motion of these leaflets causes the flow to be essentially unidirectional, mimicking the natural function of native heart valves.

The present prior art disclosure dissertation will be limited to mechanical valves, which consist of an orifice ring housing one or more leaflets. The leaflets can be flat as disclosed in U.S. Pat. No. 4,276,658-Hansen et al dated Jul. 7, 1981 and U.S. Pat. No. 4,689,046-Bokros dated Aug. 25, 1987, or curved as disclosed in U.S. Pat. No. 4,950,287-Reif dated Nov. 12, 1991. The orifice ring and leaflets are typically constructed of pyrolytic carbon or a composite of pyrolytic carbon and a substrate, such as graphite.

The design of the pivot mechanism is very important to the function of mechanical valves. It not only is responsible for the unidirectional flow characteristics, but it can also effect the dynamics of the motion of the leaflets, the wear rate of the contact surfaces, and both the homolytic and thrombogenic potential of the device. The extreme importance of these functional aspects of the design of the pivot mechanism is demonstrated by the multitude of pivot patents which have issued and the relatively few designs which have obtained long lasting clinical success.

Most pivot designs fall into three general categories: those with internal recesses in the orifice ring, those with external protrusions from the orifice ring and those with a combination of these two features. U.S. Pat. No. 4,692,165-Bokros dated Sep. 8, 1987 is an example of an external pivot design. The protrusions into the flow stream reduce the hemodynamic efficiency of the device by reducing the open area within the orifice ring available for flow. These protrusions create areas of increased local turbulence, also reducing the hemodynamic efficiency, but also creating areas of localized hemolysis. Hemolysis may be linked to thrombogenesis via the lysis of platelets. Because combination internal and external pivot designs must also have some external protrusions, these designs suffer from the same disadvantages.

The most widely used mechanical valve has an internal pivot design as disclosed in U.S. Pat. No. 4,276,658-Hansen et al dated Jul. 7, 1981. A cross-sectional view of this prior art is demonstrated in FIG. 7. Circular tabs extend radially outwardly from the sidewalls of the leaflets in an area spaced just apart from the diametrically extending surfaces of the leaflets. These tabs articulate within contoured recesses within the internal surface of the orifice ring. The contoured recesses are hour-glass shaped, formed as circular surfaces of revolution having a radius slightly larger than that of the tab on the leaflet. Corresponding, essentially mirror image, recesses are formed on the opposite internal surface of the orifice ring, allowing the counterpart tab on the opposite side of the leaflet to articulate within this recess. When the two tabs of the leaflet are properly constrained within the two recesses of the orifice ring, a pivot axis is formed. Forward flow through the valve causes the leaflets to first translate slightly (because of the generating radius of the recess is slightly larger than the radius of the tab) arid then rotate about the pivot axis, thus, fully opening the leaflets. Similarly, when the flow through valve reverses, the leaflets translate slightly and then rotate to the fully closed position. Although slight translation is unavoidable, any translation necessarily reduces the efficiency of the opening and closing dynamics of the leaflets. It not only wastes energy, but it delays the initiation of the rotational process and causes the leaflets to reach their final resting positions (either fully open or fully closed) with higher angular velocities than would be realized if no translation occurred. This results in greater impact forces within the pivot mechanism.

The contact stresses, however, depend on the impact forces and the area of the contact surfaces. As will now be demonstrated, the major undesirable feature of this disclosure is the nature of the contact surfaces between the tab of leaflet and the recess of the orifice ring. When the leaflet is in the fully open position, contact occurs between the tab of the leaflet and the recess of the orifice ring at two surfaces; surfaces A and B of the recess in FIG. 7. When the leaflet is in the fully closed position, contact occurs between the tab and the recess only at surface C of the recess. No contact occurs along surface D of the recess, because the generating radius of the recess is necessarily greater than the radius of the tab of the leaflet.

The loads exerted upon the leaflets by the hemodynamic forces generated by the heart are trivial for the case of the fully open leaflets when compared to the case of the leaflets being fully closed. Therefore, the small contact areas A and B do not give rise to significant stresses during the impact of leaflet opening. Contact area C, for the fully closed leaflet, is larger than areas A and B combined. However, since the impact loads for this case are significant, the impact stresses too may be significant. Since the generating radius of the recess is necessarily greater than the radius of the tab, no contact occurs at surface D of the recess and only half of the contact area of the tab is utilized. If contact were possible along the full length of the tab, the contact area would be doubled and the contact stress would halved. Reducing the magnitude of the contact stress is highly desirable, as it improves the durability of the pivot mechanism.

A slight variation of this concept is disclosed in U.S. Pat. No. 4,889,046-Bokros dated Aug. 25, 1987. The recess is generally an hour-glass shaped surface of revolution. The tab, however, is trapezoidal shaped. Thus, the generating curve becomes three straight lines instead of a circular arc. This disclosure suffers from the same deficiencies just described. In addition, because the surface of revolution in the recess exceeds the final resting position of the leaflet in the fully closed position, a region exists within the recess which is not mechanically washed by the motion of the tab of the leaflet. These regions of stasis within the recess are possible areas of increased thrombogenicity.

U.S. Pat. No. 4,254,508-Bokros dated Mar. 10, 1981 discloses an internal pivot design with a inverted triangular shaped recess. The first side of the triangle is adjacent to the tab of the leaflet when the leaflet is in the fully open position. The second side of the triangle is adjacent to the tab of the leaflet when the leaflet is in the fully closed position. The base of the triangle is adjacent to the inflow side of the orifice ring. No regions of stasis exist in this design. Because the recess is necessarily larger than the tab, the type of contact for the fully open leaflet is similar to the type A and B contact discussed in FIG. 7. When the leaflet is in the fully closed position, contact occurs at the base adjacent to the second side and at the first side adjacent to the second side, again like type A and B contact in FIG. 7. No contact occurs along the second side. The contact area is, thus, greatly reduced, resulting in an increase in the contact stress relative to U.S. Pat. No. 4,276,658-Hansen et al dated Jul. 7, 1981.

U.S. Pat. No. 4,996,881-Knoch et al dated Feb. 20, 1991 discloses another triangular shaped recess. The apex of the triangle is adjacent to the inflow side of the orifice. The first side of the triangle is adjacent to the tab of the leaflet when the leaflet is in the fully open position. The second side of the triangle is adjacent to the tab of the leaflet when the leaflet is in the fully closed position. No regions of stasis exist in this design either. Because the recess is necessarily larger than the tab, the type of contact for the fully open leaflet is similar to the type A and B contact discussed in FIG. 7. When the leaflet is in the fully closed position, contact occurs along the entire tab length of the second side, an improvement over U.S. Pat. No. 4,254,508-Bokros dated Mar. 10, 1981. The base of the triangular shaped recess necessarily curves away from the two sides of the recess. This is required to ensure free leaflet motion during opening and closure. The shape of the base, however, markedly increases the translational movement of the leaflets, already discussed as being an undesirable feature.

In summary, there are several disadvantages to the current prior art design configurations of pivot mechanisms in heart valve prostheses. External pivot designs are generally inferior to internal designs, because they reduce the open area within the orifice ring available for flow. This also reduces the hemodynamic efficiency of the device and may increase the hemolytic potential. Increased thrombogenisis may be linked to increased hemolysis. Some designs are inadequate because they fail to utilize the entire surface area available on the tab of the leaflet during contact with the orifice ring. This increases contact stresses and adversely affects the durability of the heart valve prosthesis. Other designs fail to mechanically wash all areas within the pivot mechanism. This may lead to increased thrombogenicity of the device. Further, some designs permit too much translation of the leaflets. This reduces the hemodynamic efficiency of the heart valve prosthesis and it increases the impact forces within the valve during both opening and closure. In addition to adversely affecting durability, heart valve prostheses with high impact forces during closure have been found to annoy patients because of their increased noise level.

SUMMARY OF THE INVENTION

A new pivot mechanism for a mechanical heart valve prostheses is disclosed which has internal recesses on the inside surface of the orifice ring. Portions of the orifice ring near the recesses are tapered to reduce flow resistance and turbulence. There are no protrusions from the inside surface of the orifice ring into the flow area. The recesses are generally triangular shaped, such that the entire length of the tabs of the leaflets contact the recesses in both the fully open and closed positions. No dead space exists and the entire recess is mechanically swept by the motion of the tabs of the leaflets. The base of the triangle is curved towards the two adjacent sides, thus, eliminating excessive translation of the leaflets.

With the foregoing in mind, it is an object of the present invention to provide a pivot mechanism for a mechanical heart valve prosthesis which utilizes internal recesses on the inside of the orifice ring with tapered portions of the orifice ring near the recesses to reduce flow resistance and minimize turbulence. This improves the hemodynamic efficiency of the heart valve prosthesis, reduces its hemolytic potential, and possibly reduces its thrombogenicity.

It is also an object of the present invention to provide a pivot mechanism for a mechanical heart valve prosthesis which enables contact between the entire length of the tabs of the leaflets and the sides of the recesses when the leaflets are in both the fully open and fully closed positions. This increases the contact area between the tabs and the recesses, reducing the magnitude of the contact stresses and, therefore, improving the durability of the device.

Another object of the present invention is to provide pivot mechanism for a mechanical heart valve prosthesis which has no regions of stasis within the recess. This reduces the thrombogenic potential of the heart valve prosthesis.

A further object of the present invention is to provide a pivot mechanism for a mechanical heart valve prosthesis which minimizes translation of the leaflets. This improves the hemodynamic efficiency of the device and it reduces the magnitude of the impact forces within the pivot mechanism, therefore, improving the durability of the device. It may also make the prothesis quieter during closure.

Other objects and advantages of the present invention will become apparent from the following detailed description, taken with reference to the accompanying drawings.

BRIEF DESCRIPTION OF THE DRAWINGS

FIG. 1 shows a top or inflow view of a mechanical heart valve prosthesis with the leaflets in the fully closed position;

FIG. 2 shows a top or inflow view of a mechanical heart valve prosthesis with the leaflets in the fully open position;

FIG. 3 shows a cross-sectional view of a mechanical heart valve prosthesis taken along line III—III as shown in FIG. 2;

FIG. 4 shows a cross-sectional view of a mechanical heart valve prosthesis taken along line IV—IV as shown in FIG. 1;

FIG. 5 shows a perspective view of a leaflet of a mechanical heart valve prosthesis;

FIG. 6 shows a perspective view of the orifice ring of a mechanical heart valve prosthesis;

DESCRIPTION OF THE PREFERRED EMBODIMENTS

Figure 7:
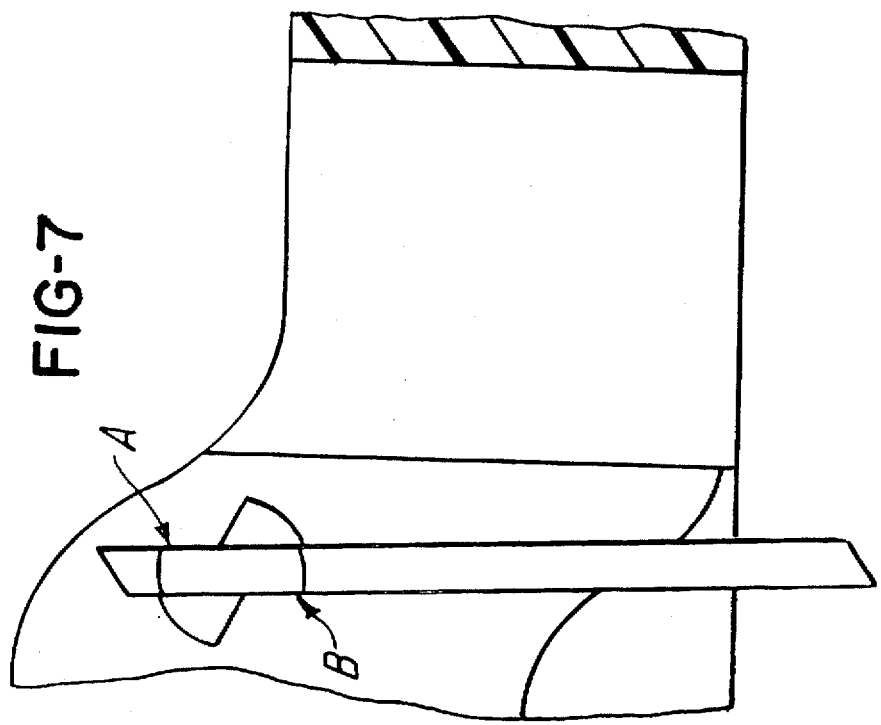
FIG. 7 shows a portion of a cross-sectional view of a mechanical heart valve prosthesis with one leaflet in the fully open position.

The following description is of the best mode presently contemplated for practicing the invention. This description is not to be taken in a limiting sense, but is made for the purpose of describing the general principles of the invention.

The scope of the invention should be determined with reference to the claims. The preferred embodiment of the present invention will now be described with reference to the accompanying drawings. In the drawings, like numerals will be used to designate like parts throughout.

FIG. 1 depicts a plan view of a bileaflet mechanical heart valve prosthesis V as seen from an inflow or top direction. A pair of leaflets 10 and 12 are housed within an annular shaped orifice ring 13. The leaflets 10 and 12 are constrained within the orifice ring 1S such that they are free to rotate within recesses P and P1 within the orifice ring 13. In this view, the leaflets 10 and 12 are shown in the fully closed position, blocking the orifice 14 in the orifice ring 13. In FIG. 2, the leaflets 10 and 12 are again shown from an inflow or top direction. However, the leaflets 10 and 12 are shown in the fully open position. The leaflets 10 and 12 have leading edges 10a and 12a that are beveled to permit a reasonably tight seal at the contact surface between the leaflets 10 and 12.

The prosthesis V is shown in cross-section in FIG. 3, with leaflets 10 and 12 fully open, and again in FIG. 4, with leaflets 10 and 12 fully closed. The leaflets 10 and 12 are depicted as flat, but they can also be curved as disclosed in U.S. Pat. No. 4,950,287-Reif dated Nov. 12 1991. The leaflets 10 and 12 have trailing edges 10b and 12b that are also beveled to permit a reasonably tight seal with the inner wall surface 18a of the orifice 14 in the orifice ring 18. The orifice ring 13 has an inflow taper 13b and an outflow taper 13c to reduce flow resistance.

The leaflet 10 is shown in a perspective view in FIG. 5. The leaflet 10 has two flat sidewalls 10c. Two essentially mirror image tabs 11 extend radially outwardly from the sidewalls 10c of the leaflet 10 in an area spaced just apart from the leading edges of the leaflet 10a. The tabs 11 have a curved portion 11a near the leading edge of the leaflet 10a and another curved portion 11b closer to the trailing edge of the leaflet 10b. Two flat or slightly curved surfaces 11c and lid of the tab 11 lie adjacent to the inflow and outflow sides of the leaflet 10, respectively.

FIG. 6 shows a perspective view of the orifice ring 13. The essentially mirror image recesses P and P1 are generally triangular shaped. The apices Pa, Pb, and Pc of the triangular recess P are curved. The two sides Pd and Pe of the triangular recess P are flat or slightly curved. The base Pf of the recess P is curved inwardly towards the two sides Pd and Pe.

Mode of Operation

The recess P within the orifice ring 13 (FIG. 6) is designed to articulate with the tab 11 of the leaflet 10 (FIG. 5). The dimensions of the recess P are slightly larger than the corresponding dimensions of the tab 11, allowing the free movement of the leaflet 10 between the fully open (FIG. 3) and the fully closed positions (FIG. 4). Surfaces 11a and 11b of the tab 11 are curved, with radii of curvature slightly less than the radii of curvature of the curved surfaces Pa, Pb, and Pc of the recess P. This also allows free rotation of the leaflet 10, improves durability, and ensures that there are no regions of stasis within the recess P.

When the leaflet 10 is in the fully open position (FIG. 3), surface Pe of the recess P (FIG. 6) is designed to mate precisely with the entire length of the tab 11, defined by the surface 11c (FIG. 5). These mating surfaces Pe and 11c may be flat or slightly curved, depending on whether the leaflet is flat or curved. Because the tab 11 is necessarily smaller than the recess P, actual contact for the fully open condition will occur with surface 11a of the tab 11 contacting surface Pb of the recess P and surface 11b of the tab 11 contacting surface Pc of the recess P. This is similar to the type A and B contact described in FIG. 7, except that curved surfaces 11a and 11b are used for contact with the recess P instead of sharp corners.

When the leaflet 10 begins to move from the fully open to the fully closed position, translation is inhibited as surface 11a of the tab 11 is brought to bear upon surface Pd of the recess P. Surface Pd of the recess is angled relative to the plane of the orifice ring such that leaflet 10 rotates with minimal translation.

Figure 8:
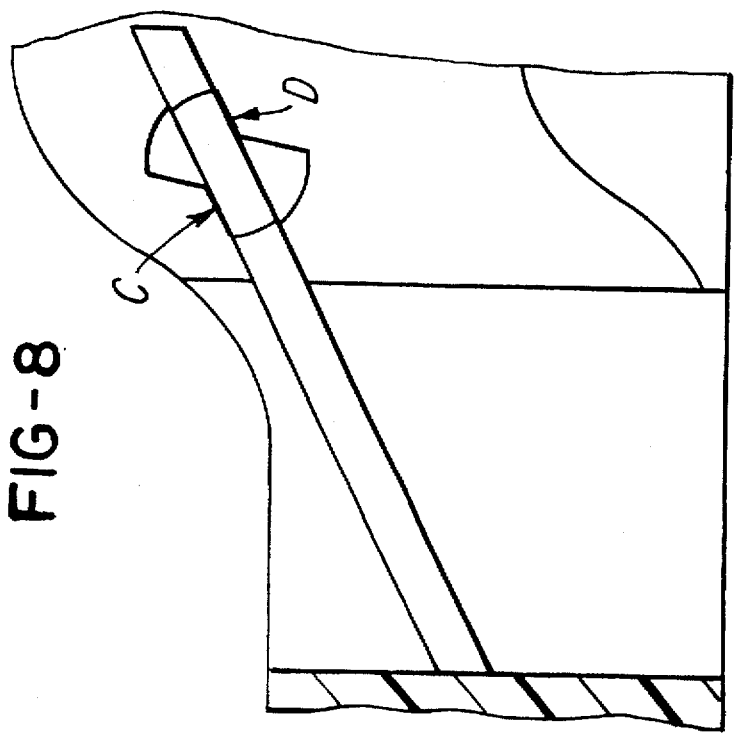
FIG. 8 shows a portion of a cross-sectional view of the mechanical heart prothesis with the other leaflet in the fully closed position.

When the leaflet 10 is in the fully closed position (FIG. 4), surface Pd of the recess P (FIG. 6) is designed to mate precisely with the entire length of the tab 11, defined by surface 11c (FIG. 5). These mating surfaces Pd and 11c may be flat or slightly curved, depending on whether the leaflet is flat or curved. Unlike some prior art, contact occurs along the entire length of the tab 11 defined by surface 11c. This is similar to the type D contact described in FIG. 8, except that contact area is increased, respectively doubled.

When the leaflet 10 moves from the fully closed to the fully open position, significant translation is again inhibited as surface 11d of the tab 11 is brought to bear upon surface Pf of the recess P. Unlike prior art, the base of the recess Pf curves inwardly towards the two sides Pd and Pe of the recess P, causing the leaflet 10 to rotate with minimal translation.

The inflow and outflow tapers 13b and 13c on the inner wall surface 13a of the orifice ring 13 permit the blood flow to pass through the orifice 14 with decreased resistance and reduced localized turbulence in these areas.

A pivot mechanism has been described which utilizes internal recesses P on the inner wall surface 13a of the orifice ring 13. The orifice ring 13 has inflow and outflow tapers 13b and 13c neat the recesses P, designed to reduce flow resistance and to reduce local turbulence. This improves hemodynamic efficiency, reduces hemolysis, and may reduce thrombogenicity. Improved contact occurs at surfaces 11a and 11b of the tab 11 as it contacts the recess P, when the leaflet is fully open. Full contact occurs along the entire length of the tab 11c as it contacts the recess P, when the leaflet 10 is fully closed. Both conditions result in increased contact surface areas, which result in reduced contact stresses and improved durability. The recess P is completely mechanically swept. This eliminates the regions of stasis and reduces the thrombogenicity of the prosthesis. The recess P is shaped such that translation of the leaflet 10 is minimized. This improves the hemodynamic efficiency, reduces the impact forces, making the device more durable and quieter.

In conclusion, the heart valve of the present disclosure represents improvements of previous heart valves including for example that of U.S. Pat. No. D-358,648Reif dated May 23, 1995 as well as being adapted for use with a heart valve rotator of Design Ser. No. 036,665-Reif filed Mar. 24, 1995 and also a heart valve locking ring of Design Ser. No. 036,662-Reif filed Mar. 24, 1995.

The present invention is, of course, in no way restricted to the specific disclosure of the specification and drawings, but also encompasses any modifications within the scope of the appended claims.

What I claim is:

1. A pivot mechanism for a mechanical heart valve prothesis having a flow area, comprising: an orifice ring having an inner wall that is tapered along portions thereof and having internal recesses on an inside surface thereof and including portions of the orifice ring near the recesses being tapered, to reduce flow resistance and turbulence without any protrusions from the inside surface of the orifice ring into the flow area to improve hemodynamic efficiency of the heart valve prosthesis, to reduce hemolytic potential thereof, and to reduce thrombogenicity thereof without any regions of stasis within the recesses, the pivot mechanism according to the foregoing in which pivotable leaflets are provided having tabs of predetermined length therewith, the, recesses being generally triangular in shape, such that entire length of tabs of the inflow side of the leaflets contact the recesses in both fully open and closed positions.

2. A pivot mechanism according to claim 1, in which the entire recess is mechanically traversed for being swept during motion of the tabs of the leaflets having a complementary fit with each of the respective recesses.

3. A pivot mechanism for a mechanical heart valve prothesis having a flow area, comprising: an orifice ring having an inner wall that is tapered along portions thereof and having internal recesses on an inside surface thereof and including portions of the orifice ring near the recesses being tapered to reduce flow resistance and turbulence without any protrusions from the inside surface of the orifice ring into the flow area to improve hemodynamic efficiency of the heart valve prosthesis, to reduce hemolytic potential thereof, and to reduce thrombogenicity thereof without any regions of stasis within the recesses, the recesses being generally triangular shaped, such that entire length of tabs of the leaflets contact the recesses in both fully open and closed positions, the base of the triangle being curved towards two adjacent sides thus eliminating excessive translation of the leaflets.

4. A pivot mechanism according to claim 3, in which the leaflets have trailing edges that are beveled to permit a reasonably tight seal with an inner wall surface of an orifice in the orifice ring having a taper as being formed on the inflow and outflow region of the inner wall to provide an inflow taper and an outflow taper to reduce flow resistance.

5. A pivot mechanism according to claim 4, in which the leaflets have leading edges two flat sidewalls, and two essentially mirror image tabs extending radially outwardly from the sidewalls of the leaflet in an area spaced just apart from the leading edges of the leaflet.

6. A pivot mechanism according to claim 5, in which the tabs have a curved portion near a respective leading edge of the leaflet and another curved portion closer to a respective trailing edge of the leaflet.

7. A pivot mechanism according to claim 6, in which two surfaces of the tab lie adjacent to the inflow and outflow sides of the leaflet, respectively.

8. A pivot mechanism according to claim 3, in which the triangular shaped recesses have curved apices.

9. A pivot mechanism for a mechanical heart valve prothesis having a flow area, comprising: an orifice ring having an inner wall that is tapered along portions thereof and having internal recesses on an inside surface thereof and including portions of the orifice ring near the recesses being tapered to reduce flow resistance and turbulence without any protrusions from the inside surface of the orifice ring into the flow area to improve hemodynamic efficiency of the heart valve prosthesis, to reduce hemolytic potential thereof, and to reduce thrombogenicity thereof without any regions of stasis within the recesses, the recesses being generally triangular shaped, such that entire length of tabs of the leaflets contact the recesses in both fully open and closed positions, two sides of the triangular recesses being slightly curved and the base of each recess being curved inwardly towards said two sides.

10. A pivot mechanism according to claim 3, in which a complementary fit for contact occurs along entire length of the tab and contact area thereof is increased.

11. A pivot mechanism according to claim 9, in which the base of the recess curves inwardly towards the two sides of the recess, causing the leaflet to rotate with minimal translation.

\* \* \* \* \*